US00PP08789P

United States Patent [19]

Austin

[11] Patent Number: Plant 8,789

[45] Date of Patent: Jun. 21, 1994

[54] SHRUB ROSE PLANT NAMED 'AUSPALE'

[75] Inventor: David C. H. Austin, Albrighton, England

[73] Assignee: Davis Austin Roses Limited, Albrighton, England

[21] Appl. No.: 40,155

[22] Filed: Mar. 30, 1993

[30] Foreign Application Priority Data

May 12, 1991 [GB] United Kingdom ..... 51395

[51] Int. Cl.[5] ..... A01H 5/00

[52] U.S. Cl. ..... Plt./1

[58] Field of Search ..... Plt. 1

*Primary Examiner*—Howard J. Locker
*Assistant Examiner*—Erich E. Veitenheimer
*Attorney, Agent, or Firm*—Klarquist Sparkman Campbell Leigh and Whinston

[57] ABSTRACT

A Rosa hybrida rose plant that is a mutation of the variety "Mary Rose" is disclosed, having pale pink flowers; Portland rose-type leaves; flat, rosette flowers; sweet, heavy fragrance; and very good repeat flowering.

1 Drawing Sheet

The present invention relates to a new and distinct variety of rose plant (Rosa hybrida) of the shrub class discovered as a spontaneous mutant of the unpatented variety "Mary Rose".

The rose plant of the present discovery differs from the parent "Mary Rose" only in its flower color, "Mary Rose" having a deep pink color, and distinguishes from all other varieties of which I am aware with the following unique combination of characteristics:

1. Pale pink flowers;
2. Portland rose-type leaves i.e., leaves usually smaller than those of a hybrid tea rose and having a non-shiny surface such as are possessed by "Comte de Chambord" and "Jacques Cartier" roses.
3. Flat, rosette flowers; and
4. Very good repeat flowering.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage: Seed and pollen parents unknown; spontaneous mutant of the "Mary Rose" variety.

Classification:

*Botanical.*—Rosa hybrida.

*Commercial.*—Shrub.

FLOWER

Observations of flower characteristics were made from specimens grown in a garden environment in Albrighton, Wolverhampton, England, in July, 1992.

Blooming habit: Recurrent.

Bud:

*Size.*—2–2.5 cm long when the petals start to unfurl.

*Form.*—Short, slightly pointed ovoid.

*Color.*—When sepals first divide, bud color is Red Group 53B/C. When half blown, the upper sides of the petals are Red Group 56D; and the lower sides of the petals are Red Group 56C.

*Sepals.*—Color: Yellow-Green Group 144A/B. Surface texture: Smooth, downy. There are three lightly appendaged sepals. There are two unappendaged sepals with smooth, downy edges.

*Receptacle.*—Color: Yellow-Green Group 144B. Shape: Goblet. Size: Small, about 8–10 mm long-×6–8 mm wide. Surface: Glandular.

*Peduncle.*—Length: Averaging about 4–5 cm. Surface: Glandular. Color: Medium green, bronzy. Strength: Stiff, erect.

Bloom:

*Size.*—Average open size is 7.0–7.5 cm in diameter.

*Borne.*—In clusters of 1 to 6 flowers having irregular shape.

*Stems.*—Medium length, normal strength. Average length is about 70–80 cm.

*Form.*—When first open: Cupped. Permanence: Outer petals curl back.

*Petalage.*—Number of petals under normal conditions: 97.

*Color.*—The upper side of the petals is Red Group 56D on the outer petals and Red Group 56B/C on the inner petals. The reverse side of the petals is Red Group 56D on the outer petals and Red Group 56B/C on the inner petals. The base of petals fades to white with yellow tip. The major color on the upper side is Red Group 56D.

*Variegations.*—None.

*Discoloration.*—The general tonality at the end of the first day: Less pink, more yellow paler. At the end of the third day: Fading to white.

*Fragrance.*—Moderate to strong, sweet, heavy.

Petals:

*Texture.*—Thin, soft.

*Shape.*—Notched, deltoid. Outer petals more round- to heart-shaped. Inner petals narrower, moderately cupped.

*Form.*—Tips slightly recurved.

*Arrangement.*—Center quartered; outer petals imbricated; inner petals caught into calyx, with medium petaloids in the center.

*Persistence.*—Outer petals drop off cleanly before drying; inner petals hang on and dry.

*Lastingness.*—On the plant: About 3–4 days. As a cut flower: About 3 days.

Reproductive parts:

*Anthers.*—Size: Medium. Quantity: Medium. Color: Yellow. Arrangement: Mixed with petaloids.

*Filaments.*—Color: Yellow.

*Pollen.*—Color: Gold yellow.

*Styles.*—Color: White/pale yellow-green.

*Stigmas.*—Color: Greenish white.

Form: Shrub.

Size: When mature, height is 120 cm, width is 120 cm.

Growth: Vigorous.

Foliage: Number of leaflets on normal mid-stem leaves: 5.

*Size.*—About 16 cm long×11 cm wide.

*Quantity.*—Normal.

*Color.*—Old foliage: Yellow-Green Group 147A. New foliage: Yellow-Green Group 144A, with reddish blush on margins and veins.

Leaflets:

*Shape.*—Pointed oval.

*Texture.*—Upper side: Leathery.

*Edge.*—Serrated.

*Serration.*—Double, small.

*Petiole rachis.*—Color: Green.

*Petiole underside.*—With 1–2 prickles per internode.

*Stipules.*—Medium to finely serrated, about 2–2.5 cm. long.

*Disease resistance.*—Resistant to mildew and blackspot under normal growing conditions at Albrighton, Wolverhampton, England.

Wood:

*New wood.*—Color: Mid-green. Bark: Smooth.

*Old wood.*—Color: Green. Bark: Smooth.

Prickles:

*Quantity.*—Ordinary number on main canes from base and on laterals from main canes.

*Form.*—Medium length, straight or slightly hooked downward.

*Color when Young.*—Red.

*Position.*—Evenly distributed around stem.

Small prickles:

*Quantity.*—Many on main stalks and on laterals.

*Color.*—Brown.

I claim:

1. A new and distinct variety of Rosa hybrida rose plant of the shrub class, substantially as herein shown and described, being a mutation of the variety "Mary Rose", and characterized particularly as to novelty by the unique combination of its pale pink flowers; Portland rose-type leaves; flat, rosette flowers; very good repeat flowering; and sweet, heavy fragrance.

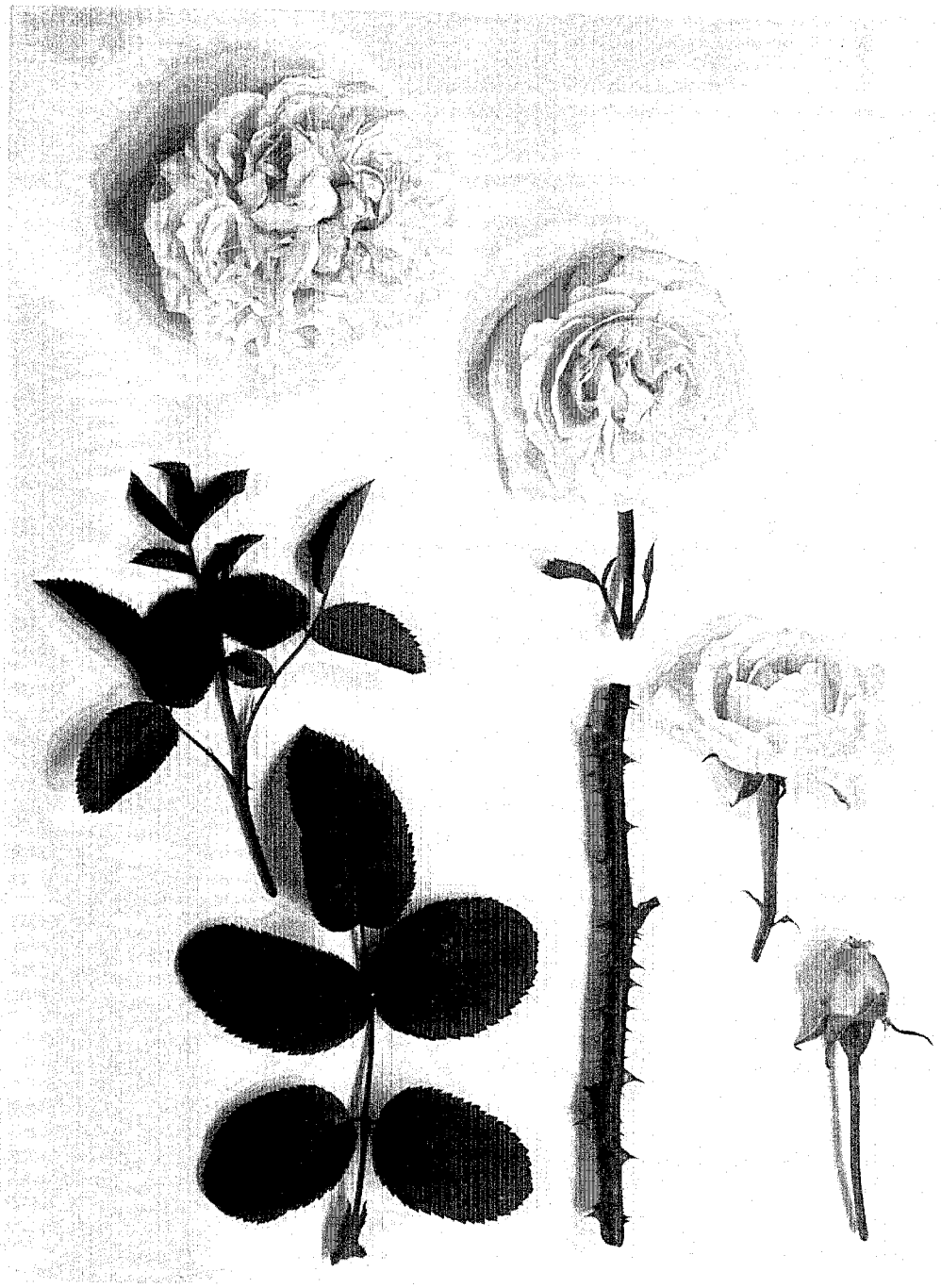

* * * * *